US008343150B2

(12) United States Patent
Artale (10) Patent No.: US 8,343,150 B2
(45) Date of Patent: Jan. 1, 2013

(54) MECHANICAL CYCLING OF SEAL PRESSURE COUPLED WITH ENERGY FOR TISSUE FUSION

(75) Inventor: Ryan C. Artale, Boulder, CO (US)

(73) Assignee: Covidien LP, Mansfield, MA (US)

( * ) Notice: Subject to any disclaimer, the term of this patent is extended or adjusted under 35 U.S.C. 154(b) by 620 days.

(21) Appl. No.: 12/503,256

(22) Filed: Jul. 15, 2009

(65) Prior Publication Data

US 2011/0015632 A1 Jan. 20, 2011

(51) Int. Cl.
*A61B 18/14* (2006.01)

(52) U.S. Cl. .......................................... 606/51; 606/52

(58) Field of Classification Search .............. 606/45–52
See application file for complete search history.

(56) References Cited

U.S. PATENT DOCUMENTS

| | | | | |
|---|---|---|---|---|
| 5,431,645 | A  * | 7/1995 | Smith et al. ...................... | 606/1 |
| 6,840,938 | B1 * | 1/2005 | Morley et al. .................... | 606/51 |
| 7,291,161 | B2 * | 11/2007 | Hooven ........................ | 606/205 |
| 7,329,256 | B2 | 2/2008 | Johnson et al. | |
| 7,491,202 | B2 | 2/2009 | Odom et al. | |
| 7,510,556 | B2 | 3/2009 | Nguyen et al. | |
| 7,513,898 | B2 | 4/2009 | Johnson et al. | |
| 7,553,312 | B2 | 6/2009 | Tetzlaff et al. | |
| 7,582,087 | B2 | 9/2009 | Tetzlaff et al. | |
| 7,799,026 | B2 * | 9/2010 | Schechter et al. .............. | 606/51 |
| 7,963,433 | B2 * | 6/2011 | Whitman et al. ........... | 227/178.1 |
| 2006/0089670 | A1 | 4/2006 | Hushka | |
| 2006/0224158 | A1 * | 10/2006 | Odom et al. ..................... | 606/51 |
| 2006/0259034 | A1 * | 11/2006 | Eder et al. ....................... | 606/50 |
| 2006/0293656 | A1 | 12/2006 | Shadduck et al. | |
| 2007/0173811 | A1 * | 7/2007 | Couture et al. ................. | 606/39 |

FOREIGN PATENT DOCUMENTS

| | | |
|---|---|---|
| CA | 2104423 | 2/1994 |
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 1159926 | 12/2001 |

(Continued)

OTHER PUBLICATIONS

International Search Report EP10169647 dated Oct. 29, 2010.

(Continued)

*Primary Examiner* — Michael Peffley (57) ABSTRACT

An electrosurgical instrument for sealing tissue includes one or more elongated shafts having an end effector assembly attached at a distal end thereof that includes a pair of opposing jaw members movable by an actuator from a first spaced apart position to a second position for grasping tissue. One or both jaw members are adapted to connect to an electrical energy source such that electrosurgical energy can be supplied to tissue disposed therebetween. A controller is coupled to the actuator for regulating a closing pressure between the jaw members and a sensor is configured to provide feedback to the controller regarding a seal pressure of tissue disposed between the jaw members.

6 Claims, 8 Drawing Sheets

FOREIGN PATENT DOCUMENTS

| | | |
|---|---|---|
| EP | 1810628 | 7/2007 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.

Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

MECHANICAL CYCLING OF SEAL PRESSURE COUPLED WITH ENERGY FOR TISSUE FUSION

BACKGROUND

1. Technical Field

The present disclosure relates to an electrosurgical instrument and method for sealing tissue. More particularly, the present disclosure relates to an endoscopic bipolar electrosurgical tool including opposing jaw members, using open or closed loop control of mechanical seal pressure before, during or after applying energy to seal tissue.

2. Background of the Related Art

Electrosurgical forceps utilize mechanical clamping action along with electrical energy to effect hemostasis on the clamped tissue. The forceps (open, laparoscopic or endoscopic) include electrosurgical sealing plates which apply the electrosurgical energy to the clamped tissue. By controlling the intensity, frequency and duration of the electrosurgical energy applied through the sealing plates to the tissue, the surgeon can coagulate, cauterize, and/or seal tissue.

Since tissue sealing procedures involve more than simply cauterizing tissue and blood, to create an effective seal the procedures involve precise control of a variety of factors. In order to affect a proper seal in vessels or tissue, it has been determined that two predominant mechanical parameters should be accurately controlled: the pressure applied to the tissue; and the gap distance between the electrodes (i.e., distance between opposing jaw members when closed about tissue).

Numerous electrosurgical instruments have been proposed in the past for various endoscopic surgical procedures. However, most of these instruments cauterize or coagulate tissue and do not allow the sufficiently strong tissue fusion of all tissue types. Consequentially, many of the existing instruments generally rely on clamping pressure alone to procure proper sealing thickness and are often not designed to take into account the seal pressure and applying energy to seal the tissue either sinusoidally or based on feedback from the tissue or properties of the device.

SUMMARY

The present disclosure is intended to overcome the drawbacks of other methods by controlling the seal pressure based on feedback including: tissue impedance, water content, temperature, device jaw opening angle, jaw temperature, jaw pressure or energy delivery. Also, the present disclosure discloses that mechanical cycling of seal pressure can be used for strong tissue fusion of tissue types that current energy based tissue fusion devices lack the ability to make.

The present disclosure relates to an electrosurgical instrument for sealing tissue, with one elongated shaft having an end effector assembly which includes a pair of opposing jaw members movable from an open position to a closed position for grasping tissue by moving one jaw member or both jaw members. The present disclosure further includes one or two jaw members being adapted to connected to an electrical energy source, an actuator coupled to one of the jaw members or each jaw member for moving the respective jaw member to the closed position for grasping tissue, a controller coupled to the actuator for regulating a closing pressure between the jaw members; and a sensor configured to provide feedback to the controller regarding the seal pressure of tissue disposed between the jaw members.

The seal pressure may be determined by various properties of the tissue disposed between the jaw members including: tissue impedance, water content of the tissue, water motility in the tissue, temperature of the tissue, temperature of at least one jaw member, jaw closure pressure and energy delivery. The seal pressure may also be determined before, during or after electrical activation of each jaw member. Further, the seal pressure may be determined in real time during electrical activation and provided to the controller for regulating the closing pressure between jaw members or the closure pressure may be cycled during electrical activation based upon a sinusoidal predetermined pressure profile to control the seal pressure. The present disclosure further provides that the electrical energy source communicates with the controller to regulate the delivery of electrical energy to tissue as a function of the seal pressure.

The present disclosure also relates to a method for sealing tissue and includes the initial step of providing an electrosurgical instrument which includes: one or more elongated shafts with an end effector assembly at a distal end of the shafts. The end effector assembly includes jaw members which are movable from an open position to a closed position for grasping tissue and at least one jaw member being adapted to connected to an electrical energy source. Further, the method includes the steps of actuating one or more jaw members to the closed position for grasping the tissue, controlling the actuator to regulate a closing pressure between the jaw members, sensing the seal pressure of tissue disposed between the jaw members, and providing feedback to the controller regarding the seal pressure of tissue disposed between the jaw members. The method may also include the steps of activating the electrical energy source to provide energy to the jaw members to seal the tissue, determining the seal pressure based on one property of the tissue disposed between the jaw members and the step of continuously sensing the seal pressure during electrical activation of one of the jaw members. The method may further include the steps of controlling the actuator to cycle the closure pressure based upon a predetermined sinusoidal pressure profile to control the seal pressure and of activating the electrical energy source as a function of the seal pressure.

Further, the present disclosure relates to a system for sealing tissue including: an electrosurgical instrument having one or more elongated shafts having an end effector assembly at a distal end thereof; an actuator coupled to one or more jaw members for moving the at least one jaw member to the closed position for grasping tissue; a controller coupled to the actuator for regulating a closing pressure between the jaw members; a sensor configured to provide feedback to the controller regarding a seal pressure of tissue disposed between the jaw members; and a generator configured to actuate the sensor and to provide feedback to the controller. The seal pressure may be determined either before, during or after electrical activation of one of the jaw members by at least one property of the tissue disposed between the jaw members including: tissue impedance, water content of the tissue, water motility in the tissue, temperature of the tissue, temperature of at least one jaw member, jaw closure pressure and energy delivery. Further, the system may include an electrical energy source to communicate with the controller to regulate the delivery of electrical energy to tissue as a function of the seal pressure.

BRIEF DESCRIPTION OF THE DRAWINGS

Various embodiments of the present disclosure will be described herein below with reference to the figures wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

An electrosurgical instrument including an end effector assembly having opposing jaw members is disclosed that is designed to fuse or seal tissue by controlling or regulating the sealing pressure during the sealing process utilizing an open or closed loop control system. A method for controlling the sealing pressure during the sealing process based on feedback from the tissue disposed between the jaw members is also disclosed.

Figure 1A:
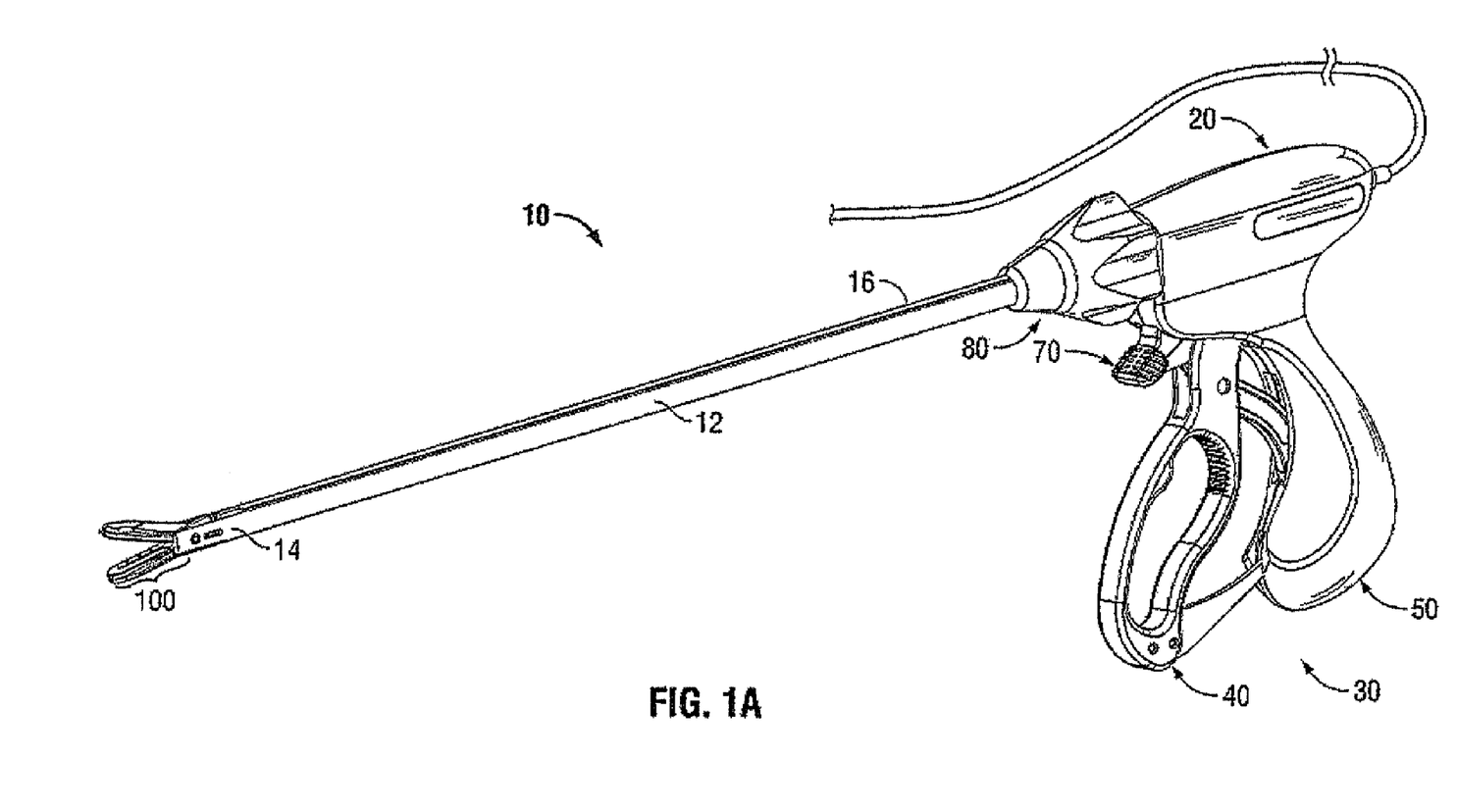
FIG. 1A is a perspective view of an endoscopic bipolar forceps in accordance with an embodiment of the present disclosure.

More particularly, and with specific reference to the figures, FIG. 1A shows an endoscopic electrosurgical forceps 10. Those skilled in the art understand that the embodiments described herein may be adapted for use with an endoscopic instrument, a laparoscopic instrument or an open instrument.

Figure 1B:
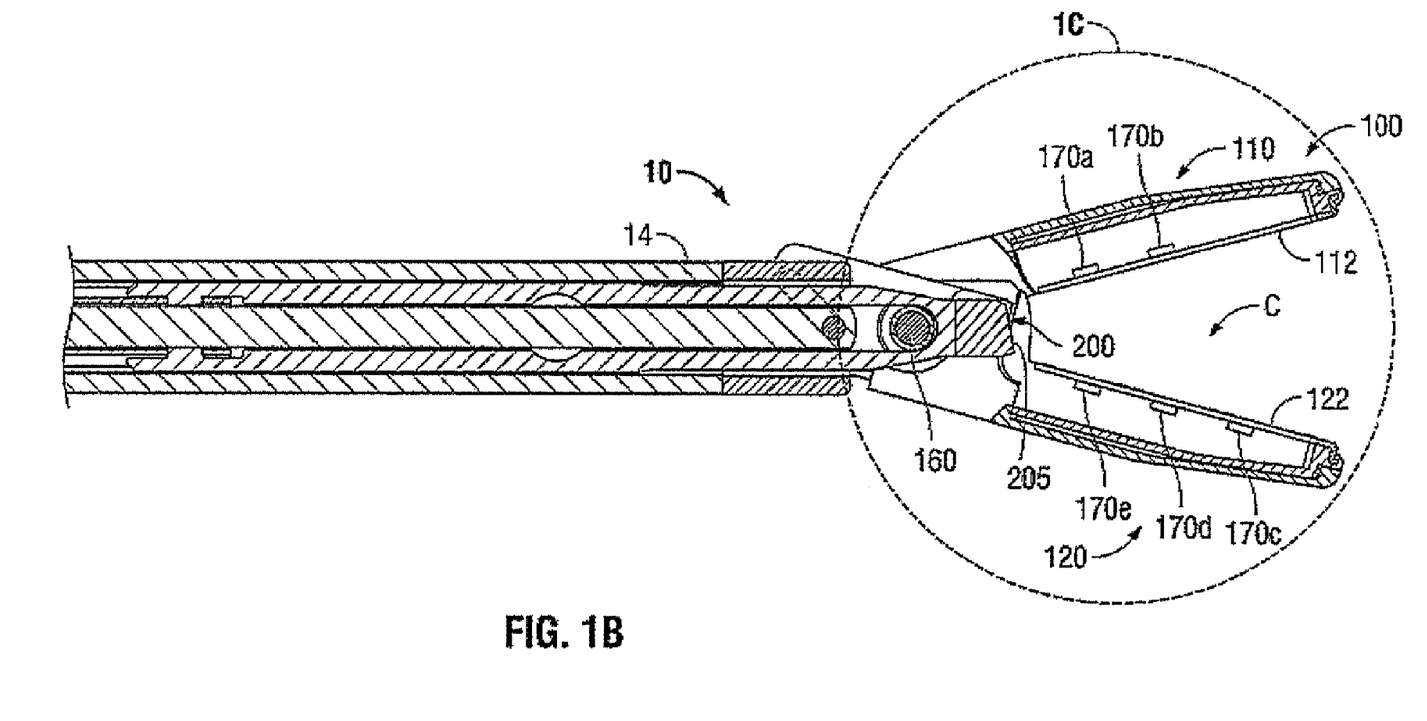
FIG. 1B is a side, partial internal view of an endoscopic forceps showing selectively adjustable stop member in accordance with an embodiment of the present disclosure.
Figure 1C:
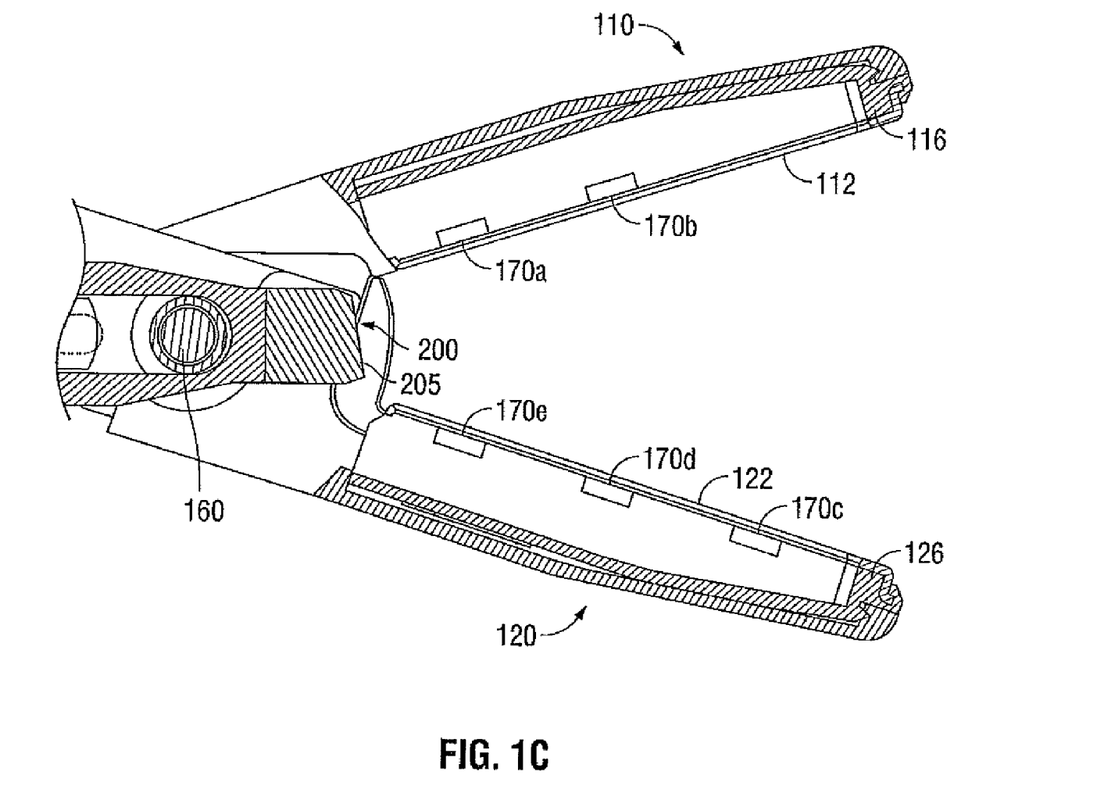
FIG. 1C is an enlarged view of the area of detail of FIG. 1B.
Figures 2, 3:
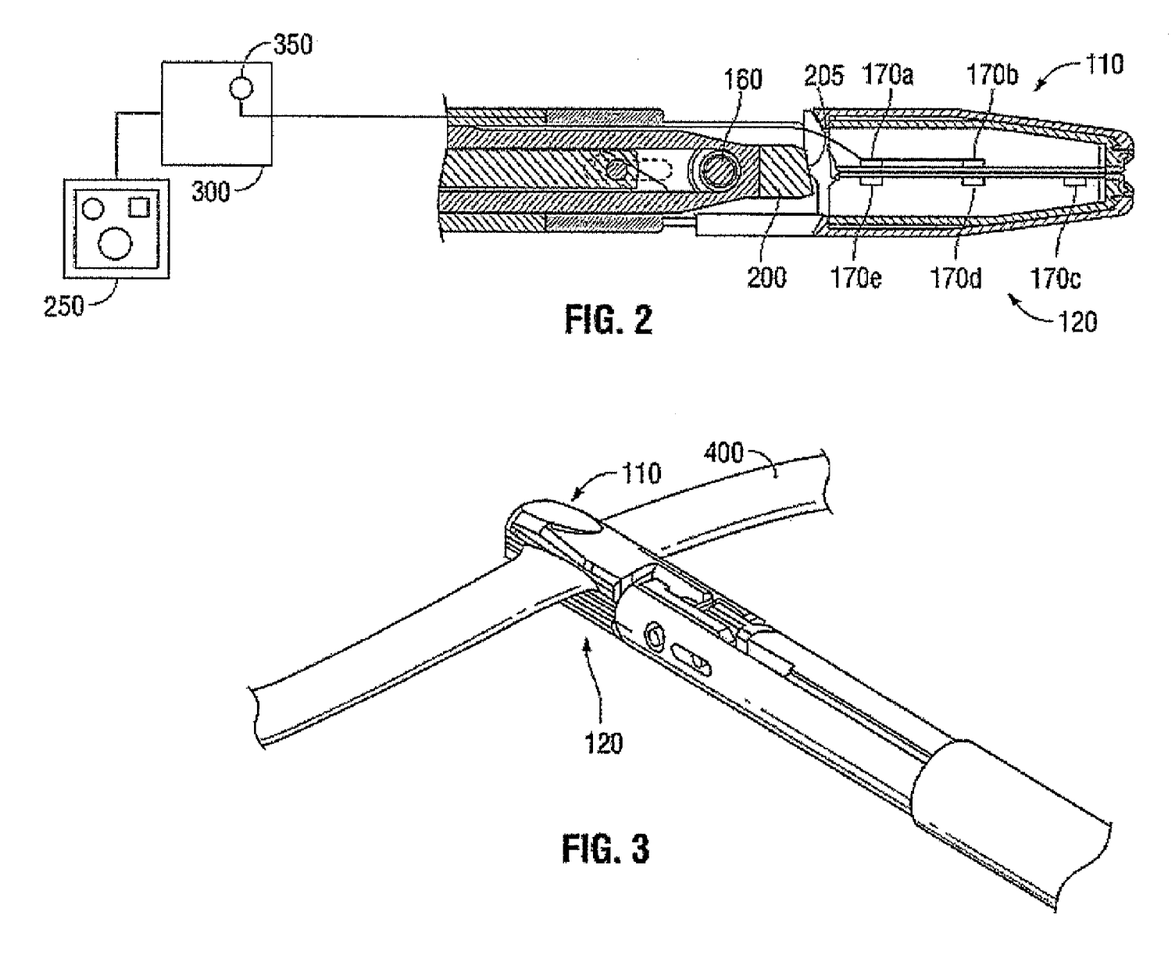
FIG. 2 is a side, partial internal view of an end effector assembly in a closed configuration.
FIG. 3 is a rear, perspective view of the end effector of FIG. 2 shown with tissue grasped therein.

FIGS. 1A-1C show the instrument 10 configured to support an effector assembly 100. More particularly, the instrument 10 generally includes a housing 20, a handle assembly 30, a rotating assembly 80, and a trigger assembly 70 that mutually cooperate with the end effector assembly to grasp, seal, and if required, divide tissue. Handle assembly 30 includes a fixed handle 50 and a movable handle 40, that moves relative to the fixed handle 50 to actuate the end effector assembly and enable a user to grasp and manipulate tissue 400 (as shown in FIG. 3). The forceps 10 also includes a shaft 12 that has a distal end 14 that mechanically engages the end effector assembly 100 and proximal end 16 that mechanically engages the housing 20 proximate the rotating assembly 80.

As shown in FIG. 2, the instrument 10 is adapted to connect to a source of electrosurgical energy, e.g., an electrosurgical generator 250 and may also connect to one or more control assemblies 300.

As seen in FIG. 1B, the end effector assembly 100 includes a pair of opposing jaw members 110 and 120 each having an electrically conductive sealing plate 112 and 122, respectively, attached thereto for conducting electrosurgical energy through tissue 400 held between the jaw members. More particularly, the jaw members 110 and/or 120 move in response to movement of the handle 40 from an open position to a closed position. For instance, either jaw member 110 or jaw member 120 may move in response to movement of the handle 40 from an open position to a closed position or both jaw members 110 and 120 may move in response to movement of the handle 40 from an open position to a closed position. In the open position the sealing plates 112 and 122 are disposed in spaced relation relative to one another. In a clamped or closed position the sealing plates 112 and 122 cooperate to grasp tissue, and apply electrosurgical energy thereto.

The jaw members 110 and 120 are activated using a drive assembly (not shown) enclosed within the housing 20. The drive assembly cooperates with the movable handle 40 to impart movement of the jaw members 110 and/or 120 from the open position to the clamping or closed position. Examples of a handle assemblies are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 (now U.S. Pat. No. 7,156,846) entitled "VESSEL SEALER AND DIVIDER FOR USE WITH SMALL TROCARS AND CANNULAS.

In addition, the handle assembly 30 of this particular disclosure includes a four-bar mechanical linkage that provides a unique mechanical advantage when sealing tissue between the jaw members 110 and 120. For example, once the desired position for the sealing site is determined and the jaw members 110 and 120 are properly positioned, handle 40 may be compressed fully to lock the electrically conductive sealing plates 112 and 122 in a closed position against the tissue. The details relating to the inter-cooperative relationships of the inner-working components of forceps 10 are disclosed in the above-cited, commonly-owned U.S. patent application Ser. No. 10/369,894. Another example of an endoscopic handle assembly that discloses an off-axis, lever-like handle assembly, is disclosed in the above-cited U.S. patent application Ser. No. 10/460,926 (now U.S. Pat. No. 7,156,846). When the handle is fully actuated and locked, the jaw members 110 and 120 provide a specific closure pressure to tissue to facilitate tissue sealing. Typically, the initial sealing pressure is between about 3 kg/cm$^2$ to about 16 kg/cm$^2$. As explained in more detail below, during activation an array of sensors 170a-170e provide feedback to a control assembly 600 that regulates the pressure on tissue during the sealing process.

Figure 4:
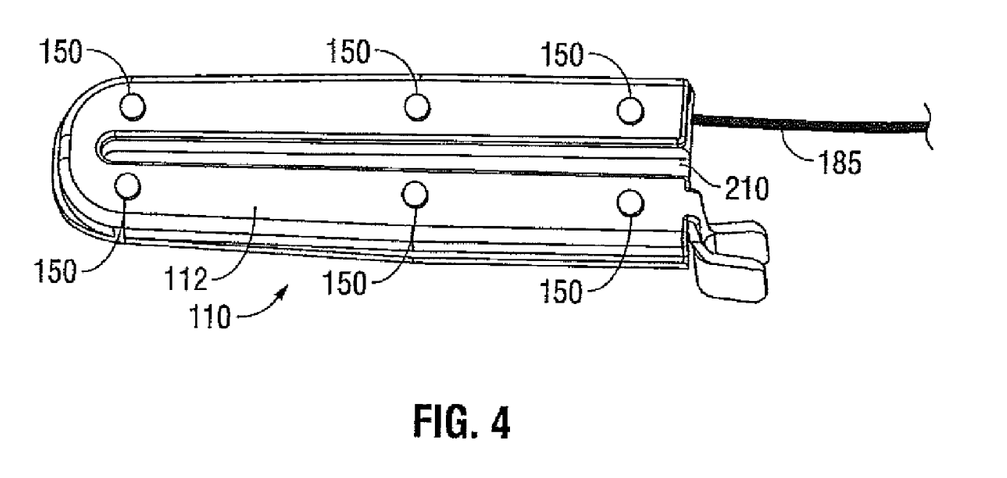
FIG. 4 is an enlarged, perspective view of an electrically conductive sealing plate of the end effector assembly.

As shown in FIGS. 1A-1C, the electrosurgical instrument 10 also includes a trigger 70 that advances a knife 200 disposed within the end effector assembly 100. Once a tissue seal is formed, the user activates the trigger 70 to separate the tissue 400 along the tissue seal utilizing a cutting edge 205 of the knife 200. FIG. 4 shows a longitudinally-oriented channel 210 defined in an electrically conductive sealing plate 112 extending from the proximal end to the distal end thereof. The channel 210 facilitates longitudinal reciprocation of the knife 200 along a preferred cutting plane to effectively and accurately separate the tissue 400 along a formed tissue seal.

The forceps 10 also includes a rotating assembly 80 mechanically associated with the shaft 12 and the drive assembly (not shown), Movement of the rotating assembly 80 imparts similar rotational movement to the shaft 12 which, in turn, rotates the end effector assembly 100. Various features along with various electrical configurations for the transference of electrosurgical energy through the handle assembly 20 and the rotating assembly 80 are described in more detail in the above-mentioned commonly-owned U.S. patent application Ser. Nos. 10/369,894 and 10/460,926 (now U.S. Pat. No. 7,156,846).

As best seen with respect to FIGS. 1A-2, the end effector assembly 100 attaches to the distal end 14 of shaft 12. The jaw members 110 and 120 are pivotable about a pivot 160 from the open to closed positions upon relative reciprocation, i.e., longitudinal movement, of the drive assembly (not shown). Again, mechanical and cooperative relationships with respect to the various moving elements of the end effector assembly 100 are further described by example with respect to the above-mentioned commonly-owned U.S. patent application Ser. Nos. 10/369,894 and 10/460,926 (now U.S. Pat. No. 7,156,846).

As shown in FIG. 3, the electrically conductive plates 112 and 122 cooperate to seal tissue 400 held between the jaw members 110 and 120 upon the selective application of electrosurgical energy. Jaw members 110 and 120 also include insulators 116 and 126, which together with the outer, non-conductive plates of the jaw members 110 and 120 are configured to limit and/or reduce many of the known undesirable effects related to tissue sealing, e.g., flashover, thermal spread and stray current dissipation as shown in FIG. 1C.

It is envisioned that the forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 20 and handle assembly 30. In either of these two instances, the forceps 10 may be either partially disposable or reposable, such as where a new or different end effector assembly 100 or end effector assembly 100 and shaft 12 are used to selectively replace the old end effector assembly 100 as needed.

As shown in FIG. 4, the sealing surfaces may include one or more stop members 150 configured to limit the movement of the two opposing jaw members 110 and 120 (and sealing plates 112 and 122) relative to one another to form a gap therebetween (see FIG. 4). It is envisioned that the stop members 150 may be disposed on one or both of the sealing plates 112 and 122 depending upon a particular purpose or to achieve a particular result. Sealing plate 112 may be electrically coupled to a terminal or 350 of the control assembly 300 via cable 185. Although not shown, sealing plate 122 may also be coupled to a terminal 350 of the control assembly 300.

Since the instrument 10 applies energy through electrodes, each of the jaw members 110 and 120 includes an electrically conductive sealing plate 112 and 122, respectively, disposed on an inner-facing surface thereof. Thus, once the jaw members 110 and 120 are fully compressed about the tissue 400, the user simply activates the forceps 10 to seal tissue.

As best shown in FIGS. 1B-2, an array of sensors 170a-170e are positioned within a cavity "C" defined in jaw members 110 and 120. The sensors 170a-170e are configured to automatically sense various properties of the tissue disposed between the jaw members 110 and 120 and provide feedback to the control assembly 300 during the sealing process. Such properties include, but are not limited to: tissue impedance, tissue type, tissue clarity, tissue compliance, temperature of the tissue or jaw members, water content in tissue, jaw opening angle, water motility in tissue, energy delivery, jaw closure pressure. The control assembly 300 is coupled to a pressure controller 500 (see FIG. 5) that regulates and adjusts the closing pressure between the jaw members 110 and 120 during the sealing process to enhance the tissue seal.

The instrument 10 determines the seal pressure on tissue 400 based upon various properties of the tissue 400 disposed between the jaw members 110 and 120 including: tissue impedance, tissue type, tissue clarity, tissue compliance, temperature of the tissue or jaw members, water content in tissue, jaw opening angle, water motility in tissue, energy delivery, jaw closure pressure, etc. Based upon such properties, the seal pressure may be determined either before, during or after electrical activation of at least one jaw member in real time during electrical activation.

As seen in FIG. 3, the sensors 170a-170e may be coupled to the control assembly via an open loop or closed loop feedback system to regulate the seal pressure on the tissue between the jaw members 110 and 120. It is important to note that the closure pressure of the jaw members 110 and 120 correlates to, but is not necessarily the same as, the sealing pressure on the tissue 400 disposed between the jaw members 110 and 120. The sensors 170a-170e measure the sealing pressure on the tissue 400 and relay the sealing pressure information back to the control assembly 300 which operatively communicates with a pressure controller 500 to adjust the sealing pressure based upon the information provided by sensors 170a-170e and the desired sealing pressure according to a predetermined seal pressure profile.

Figure 5:
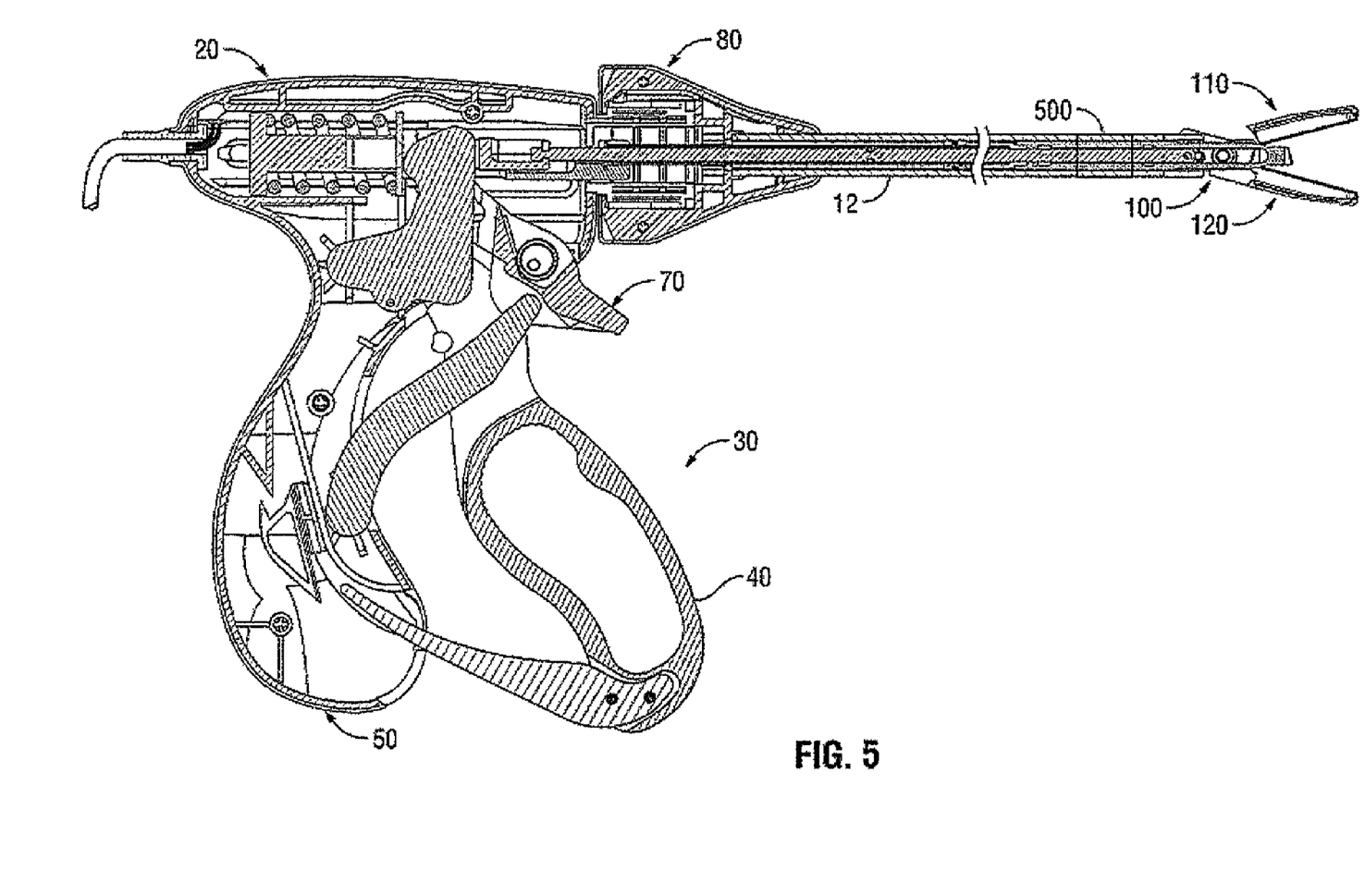
FIG. 5 is a slightly-enlarged, cross-section of the forceps showing the internal working components of the housing.

As best seen in FIG. 5, a pressure controller 500 is operatively coupled to the shaft 12 of the forceps 10. Pressure controller 500 may be any type of electrical, or electro-mechanical mechanism that provides additional force on the drive assembly (not shown) to increase or decrease the closure pressure of the jaw members 110 and 120 which, in turn, increases or decreases the seal pressure on the tissue disposed therebetween. For example, a servo motor, gear assembly, hydraulic mechanism, worm drive, etc. may be coupled to the shaft 12 and operatively coupled to the drive assembly (not shown) to provide additional force to the drive assembly (not shown) as per the information.

As mentioned above, in one embodiment, the initial closure pressure between the jaw members 110 and 120 upon actuation of the handle assembly 30 and locking of the moveable handle 40 relative to the fixed handle 50 is about 3 kg/cm$^2$ to about 16 kg/cm$^2$. The sealing pressure on the tissue 400 may or may not fall within this range. The sensors 170a-170e may be configured to initially determine the sealing pressure on tissue prior to initial activation of the forceps. For example, the sensors 170a-170e may determine that additional force needs to be provided to the drive assembly (not shown) to increase the closure pressure of the jaw members 110 and 120 which, in turn, increases the sealing pressure of the tissue 400. As mentioned above, the sealing pressure may be determined by tissue impedance, tissue type, tissue clarity, tissue compliance, temperature of the tissue or jaw members, water content in tissue, jaw opening angle, water motility in tissue, energy delivery, etc.

The appropriate sealing pressure for initial activation may be based upon a predetermined pressure profile stored within the generator 250 or control assembly 300, which may be based on tissue type, tissue temperature, tissue size, etc. If more or less sealing pressure on tissue is required, the control assembly 300 communicates with the pressure controller 500 to regulate the closure force of the jaw members 110 and 120. For example, while the handle 40 is locked relative to fixed handle 50, the pressure controller 500 may be configured to provide +/−10 kg/cm$^2$ when required to match a predetermined pressure profile or pressure algorithm.

During the sealing process, the sensors 170a-170e, control assembly 300 and pressure controller 500 all cooperate to regulate the sealing pressure on tissue to conform to a predetermined pressure profile or pressure algorithm. For example, the pressure controller 500 may be instructed by the control assembly 300 to increase the closure pressure on the jaw members 110 and 120 (which increases the sealing pressure on tissue 400) due to the tissue shrinking during the sealing process. Moreover, the seal pressure may be cycled during electrical activation based upon a predetermined sinusoidal pressure profile to enhance the tissue seal. The sensors 170a-170e may interact sequentially, simultaneously or in another manner to sense feedback from the tissue and determine the sealing pressure.

As seen in FIG. 3, the sensors 170a-170e may use an open or closed loop feedback system to regulate the closing pressure between the jaw members 110 and 120 or the closure pressure may be cycled during electrical activation based upon a predetermined sinusoidal pressure profile. In one embodiment, the sensors 170a-170e may cooperate in various ways or configurations including along the surface where the proximal sensor provides feedback to the distal sensor to regulate the closing pressure. Alternatively, the sensors 170a-170e on one jaw member may cooperate with sensors on the opposite jaw member to regulate the closing pressure. Further, a plurality of sensors along the ceiling may cooperate with one another or opposing sensors.

The procedure may be automated using a series of sensors 170a-170e, control assembly 300 and pressure controller 500. The sealing pressure control system described herein is believed to provide more effective sealing of tissue especially large tissue structures, such as lung tissue. In the automated system, the sealing pressure on the tissue is monitored and adjusted during activation based upon a continually-sensed surgical condition from the sensors relating to any one or more of a series of tissue parameters (e.g., tissue impedance, tissue type, tissue clarity, tissue compliance, temperature of the tissue or jaw members, water content in tissue, jaw opening angle, water motility in tissue, energy delivery, etc). utilizing an open or closed feed back control loop. The pressure controller 500 may be manual, where the gauge instructs user through a visual or audible indicator to increase or decrease the closure pressure on the jaw to in turn adjust the sealing pressure on the tissue.

Figure 6:
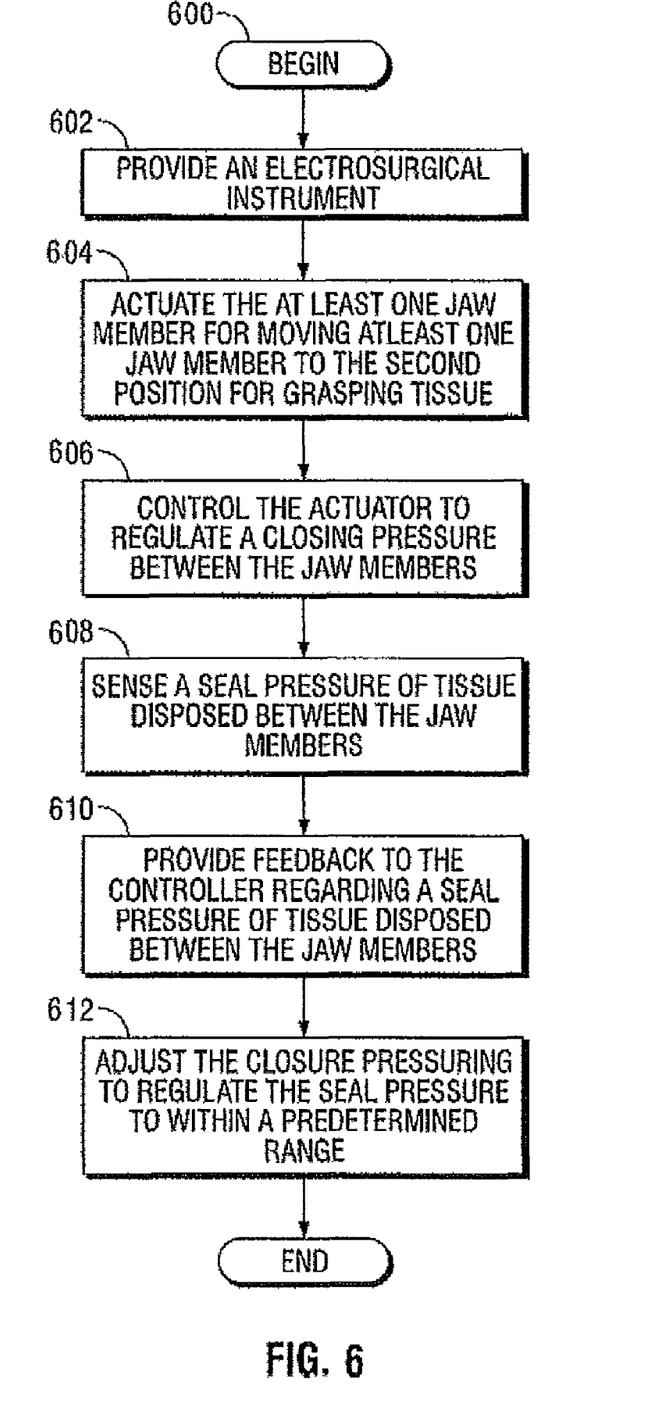
FIG. 6 shows a flow chart showing a sealing method using the electrosurgical instrument of FIGS. 1A-4.

As shown in FIG. 6, a method for sealing tissue using the forceps 10 is also disclosed herein that includes the initial step 602 of providing an electrosurgical instrument, e.g., forceps 10, including one or more shafts 12 having an end effector assembly 100 at a distal end thereof, the end effector assembly 100 including a pair of opposing jaw members 110 and 120 movable from a first spaced apart position to a second position for grasping tissue. At least one jaw member, e.g., 110 is adapted to connect to an electrical energy source. In step 604, at least one jaw member 110 is actuated to the second position for grasping tissue 400. The closing pressure between the jaw members is regulated by controlling the actuator in step 606. The instrument 10 senses a seal pressure of tissue 400 disposed between the jaw members 110 and 120 in step 608 and provides feedback to the control assembly 300 regarding the seal pressure of tissue 400 disposed between the jaw members 110 and 120. In step 612, the pressure controller 500 adjusts the closing pressure to regulate the seal pressure of the jaw members 10 and 120 on the tissue 400 during the sealing process to within a predetermined range.

The seal pressure of the tissue 400 may be determined by one or more sensors 170a-170e that measure one or more properties of the tissue 400 disposed between the jaw members 110 and 120, including: tissue impedance, tissue type, tissue clarity, tissue compliance, temperature of the tissue or jaw members, water content in tissue, jaw opening angle, water motility in tissue, energy delivery, etc.

In one method, the seal pressure may be determined prior to initial activation of the forceps, continually-sensed during the sealing process and/or after activation to determine seal quality. The seal pressure may be regulated according to a seal pressure profile (e.g., sinusoidal) or seal pressure algorithm. Moreover, the seal pressure may be cycled during electrical activation based upon a predetermined pressure profile or pressure algorithm.

Figures 7A, 7B:
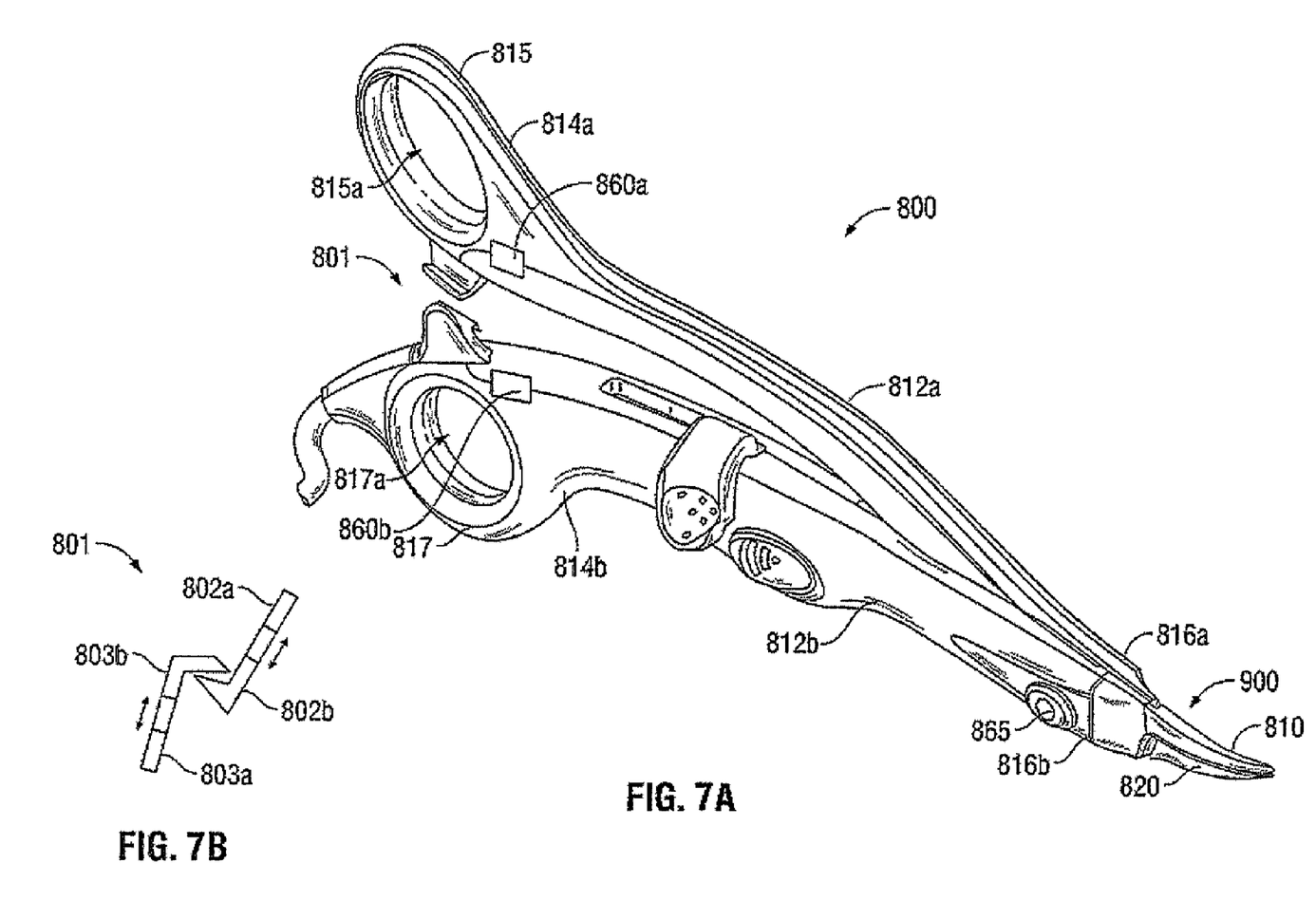
FIG. 7A is a perspective view of an open bipolar forceps which is configured to close according to the present disclosure.
FIG. 7B is a side view of a ratchet mechanism of the open bipolar forceps shown in FIG. 7A.

FIG. 7A shows an open forceps 800 for use in accordance with the present disclosure. Forceps 800 includes a pair of opposing shafts 812a and 812b having an end effector assembly 900 attached to the distal ends 816a and 816b thereof, respectively. End effector assembly 900 is similarly in design to end effector assembly 100 and includes pair of opposing jaw members 810 and 820 that are pivotably connected about a pivot pin 865 and which are movable relative to one another to grasp tissue. Each shaft 812a and 812b includes a handle 815 and 817, respectively, disposed at the proximal end 814a and 814b thereof which each define a finger hole 815a and 817a, respectively, therethrough for receiving a finger of the user. Finger holes 815a and 817a facilitate movement of the shafts 812a and 812b relative to one another which, in turn, pivot the jaw members 810 and 820 from an open position wherein the jaw members 810 and 820 are disposed in spaced relation relative to one another to a clamping or closed position wherein the jaw members 810 and 820 cooperate to grasp tissue therebetween. In a similar fashion to the embodiments described above, an array of sensors 170a-170e may be disposed within each respective jaw members 810 and 820.

A ratchet mechanism 801 is disclosed at the proximal end of the forceps 800 that is configured to maintain the jaw members 110 and 120 in a closed configuration for grasping tissue 400. Much like the forceps 10, the ratchet mechanism 801 is designed to initially maintain a predetermined initial closing pressure on the jaw members 810 and 820, e.g., between about 3 kg/cm$^2$ to about 16 kg/cm$^2$. As best shown in FIG. 7B, the ratchet mechanism 801 includes opposing mechanical interfaces 802b and 803b that are configured to engage one another upon relative movement therebetween and lock the jaw members 810 and 820 in a closed orientation about tissue 400. The ratchet mechanism 801 also includes telescopic elements 802a and 803a that telescopically receive the corresponding opposing mechanical interfaces 802b and 803b to allow adjustment of the two opposing mechanical interfaces 802b and 803b relative to one another.

Control assemblies 860a and 860b are disposed in respective shaft members 812a and 812b and are configured to communicate with the sensors 170a-170e to determine the sealing pressure of the tissue 400 disposed between jaw members 810 and 820. In this instance, the control assemblies 860a and 860b may include pressure control mechanisms disposed therein that are configured to control the telescopic engagement of the mechanical interfaces 802b and 803b within the telescopic elements 802a and 803a, which, in turn, regulates the closure pressure between jaw members 810 and 820 and the sealing pressure on the tissue 400.

As mentioned above, the initial closure pressure between the jaw members 810 and 820 upon actuation and locking of the shafts 812a and 812b may be about 3 kg/cm$^2$ to about 16 kg/cm$^2$. The sensors 170a-170e may be configured to initially determine the sealing pressure on tissue 400 prior to initial activation of the forceps 800. For example, the sensors 170a-170e may determine that additional force needs to be provided to the control assemblies 860a and 860b to increase the closure pressure of the jaw members 810 and 820 which, in turn, increases the sealing pressure of the tissue 400. The sealing pressure may be determined by tissue impedance, tissue type, tissue clarity, tissue compliance, temperature of the tissue or jaw members, water content in tissue, jaw opening angle, water motality motility in tissue, energy delivery, etc.

The appropriate sealing pressure for initial activation may be based upon a predetermined pressure profile stored within the generator 250 or control assemblies 860a and/or 860b which may be based on tissue type, tissue temperature, tissue size, etc. If more or less sealing pressure on tissue is required, the control assemblies 860a and 860b communicate with the pressure controller (disposed within the control assemblies 860a and 860b in this instance) to regulate the closure force of the jaw members 810 and 820. For example, the control assemblies 860a and 860b may be configured to provide +/−10 kg/cm² when required to match a predetermined pressure profile or pressure algorithm.

During the sealing process, the sensors 170a-170e and the control assemblies 860a and 860b cooperate to regulate the sealing pressure on tissue 400 to conform to a predetermined pressure profile or pressure algorithm. Moreover, the seal pressure may be cycled (e.g., like in an open loop feedback system) during electrical activation based upon a predetermined sinusoidal pressure profile to enhance the tissue seal. In a closed loop system, the seal pressure may be controlled based on feedback from one or more continually-sensed surgical conditions e.g., tissue impedance, tissue type, tissue clarity, tissue compliance, temperature of the tissue or jaw members, water content in tissue, jaw opening angle, water motility in tissue, energy delivery, etc. The sealing pressure on the tissue may be adjusted before, during or after activation based upon the feedback from the open or closed loop feedback system.

From the foregoing, and with reference to the various figure drawings, those skilled in the art will appreciate that certain modifications can also be made to the present disclosure without departing from the scope of the same. While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument for sealing tissue, comprising:
    an end effector assembly including a pair of opposing jaw members, at least one of the jaw members adapted to move from a first position to a second position for grasping tissue, at least one of the jaw members adapted to connect to an electrical energy source;
    an actuator coupled to at least one jaw member for moving the at least one jaw member to the second position for grasping tissue; and
    a controller configured to control the actuator to regulate a closing pressure between the jaw members;
    wherein the controller cycles the closing pressure during electrical activation based upon a predetermined pressure profile to control a sealing pressure.

2. An electrosurgical instrument for sealing tissue according to claim 1, wherein the controller includes a pressure controller for regulating the sealing pressure of tissue disposed between the jaw members to within about ±10 kg/cm².

3. An electrosurgical instrument for sealing tissue according to claim 1, wherein the predetermined pressure profile is sinusoidal.

4. A method of sealing tissue comprising the steps of:
    providing an electrosurgical instrument including:
        an end effector assembly including a pair of opposing jaw members;
        an actuator coupled to at least one jaw member for grasping tissue; and
        a controller configured to control the actuator to regulate a closing pressure between the jaw members;
    actuating the actuator to move at least one jaw member to grasp tissue; and
    controlling the actuator to regulate the seal pressure of the jaw members on tissue by cycling the closing pressure during electrical activation based upon a predetermined pressure profile.

5. A method of sealing tissue according to claim 4, the method further comprising:
    activating an electrosurgical energy source to supply energy to tissue disposed between the jaw members.

6. A method of sealing tissue according to claim 4, wherein the step of controlling the actuator is based upon a predetermined sinusoidal pressure profile.

* * * * *